United States Patent [19]
Kranys

[11] Patent Number: 5,833,659
[45] Date of Patent: *Nov. 10, 1998

[54] INFUSION BALLOON CATHETER

[75] Inventor: Rudy J. Kranys, Coconut Groves, Fla.

[73] Assignee: Cordis Corporation, Miami Lakes, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 678,003

[22] Filed: Jul. 10, 1996

[51] Int. Cl.⁶ ................................................. A61M 29/00
[52] U.S. Cl. ............................................. 604/96; 604/101
[58] Field of Search ........................... 604/96, 101, 102; 606/192, 194

[56] References Cited

U.S. PATENT DOCUMENTS

| | | |
|---|---|---|
| 4,581,017 | 4/1986 | Sahota . |
| 4,762,129 | 8/1988 | Bonzel . |
| 4,944,745 | 7/1990 | Sogard et al. . |
| 5,040,548 | 8/1991 | Yock . |
| 5,087,244 | 2/1992 | Wolinsky et al. . |
| 5,232,444 | 8/1993 | Just et al. . |
| 5,792,106 | 8/1998 | Mische ...................................... 604/96 |

*Primary Examiner*—Wynn Wood Coggins
*Assistant Examiner*—Cris L. Rodriguez
*Attorney, Agent, or Firm*—Michael W. Montgomery

[57] ABSTRACT

Apparatus and method is disclosed relating to a rapid exchange perfusion and infusion balloon catheter for treating a blood vessel with a treatment fluid. A guide catheter allows the balloon catheter to be inserted into the subject and placed near a treatment region within the vascular system. A fluid source is used to selectively inflate an infusion balloon. A guide wire tube having perfusion holes and extending through the balloon allows continuous blood flow while the balloon is inflated. An exit spaced along the guide wire tube allows the infusion balloon catheter to be rapidly exchanged with another infusion balloon catheter without having to remove the guide wire from its position within the subject.

17 Claims, 3 Drawing Sheets

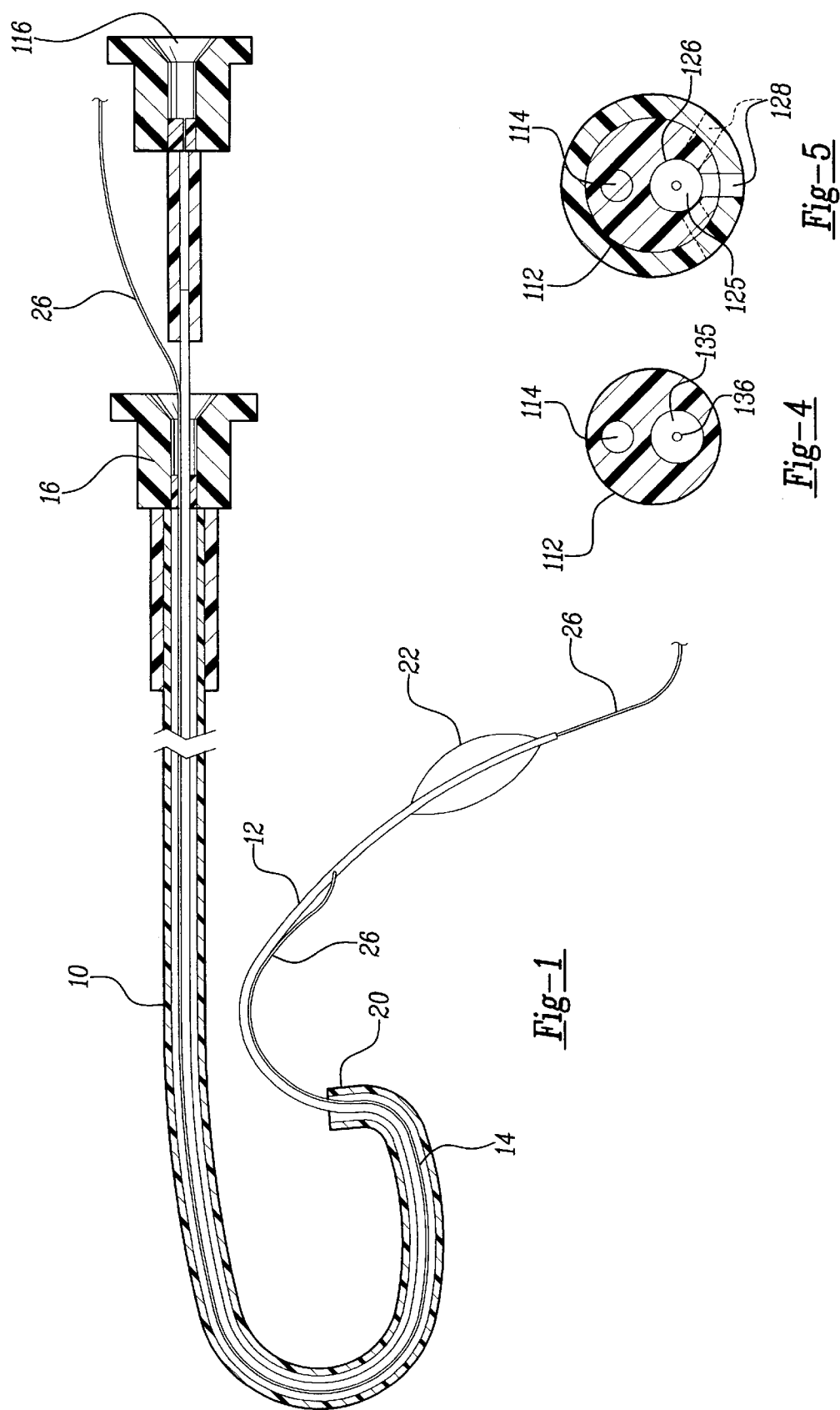

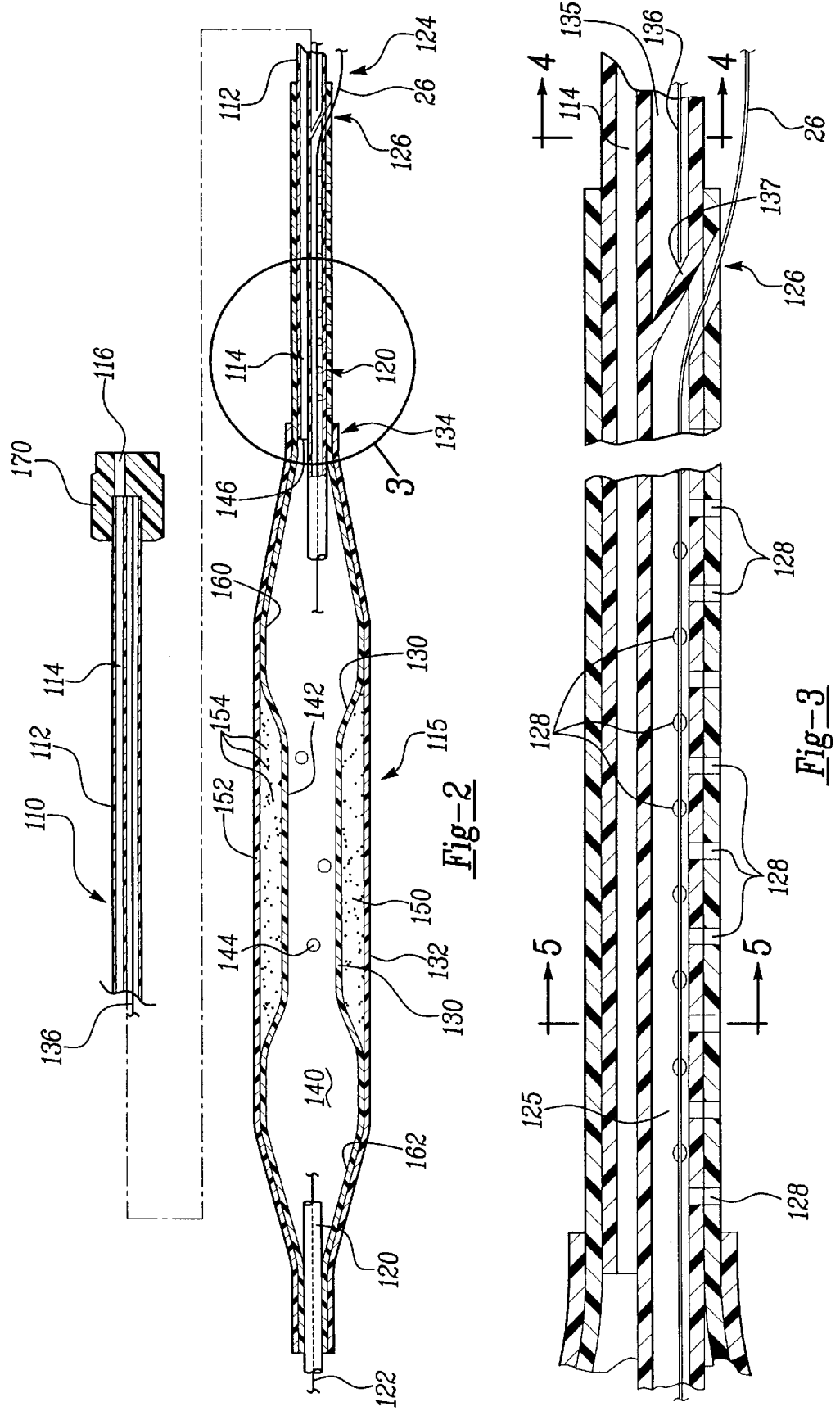

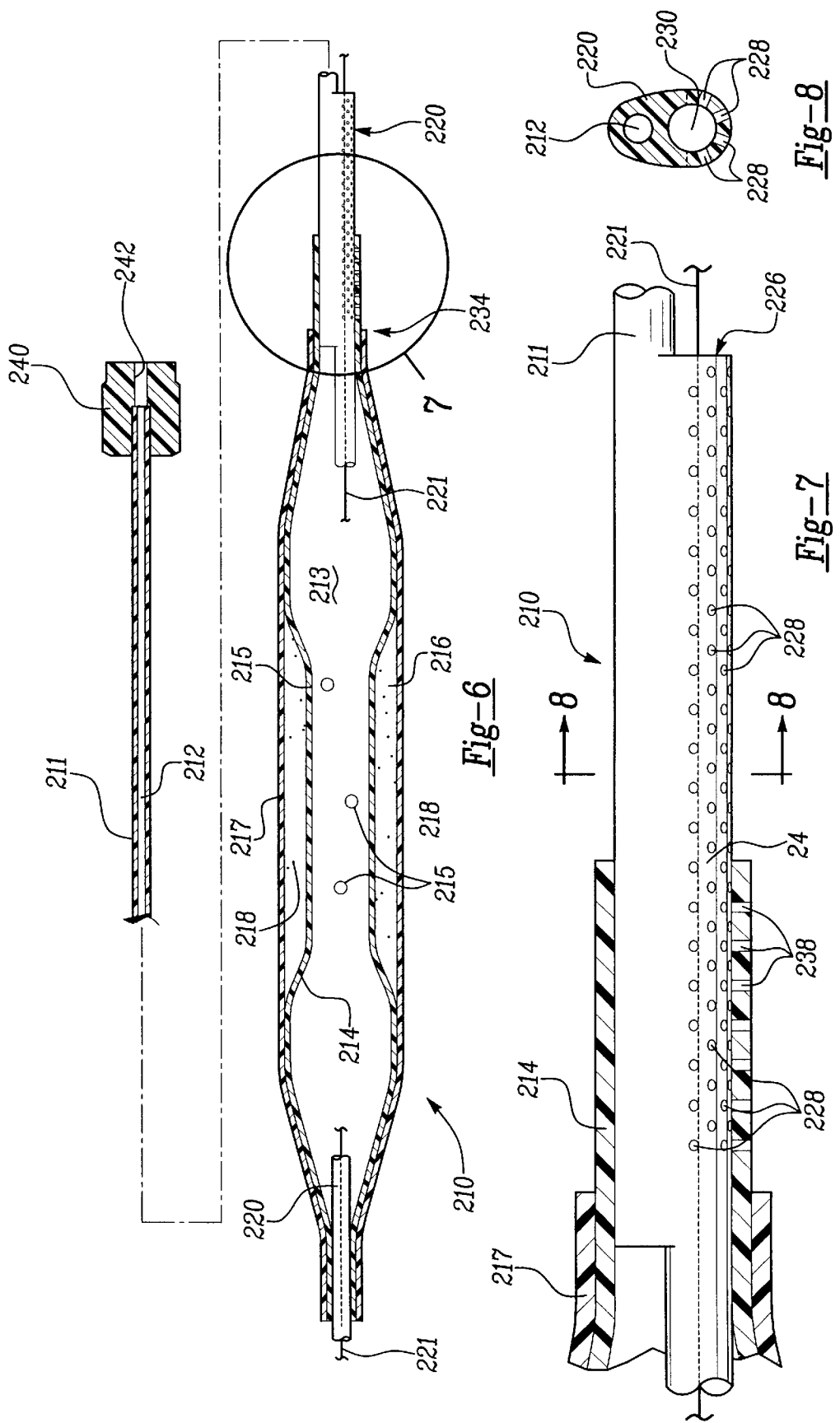

INFUSION BALLOON CATHETER

FIELD OF THE INVENTION

The present invention concerns an infusion balloon catheter having an infusion balloon for delivering a treatment fluid to a treatment site within a subject while allowing blood flow past the infusion balloon.

BACKGROUND ART

Catheterization procedures are well known for diagnosis and treatment of lesions in the cardiovascular system. One such catheterization procedure is known as angioplasty and is used to reduce the damaging effects of vascular plaque blockage or constriction in a subject blood vessel.

In an angioplasty procedure, an expandable balloon is introduced into the patient's arterial system and advanced until it is positioned in the region of the blockage or constriction. Once the balloon is properly positioned, it is expanded by filling it with a liquid. In successful procedures, the expandable balloon presses outwardly against the walls of the artery and expands the artery to increase blood flow.

Infusion catheters are catheters having an infusion balloon designed to deliver a treatment fluid to a treatment site within a blood vessel. The infusion balloon is placed at a subject treatment site in a manner similar to the process of placing a dilation catheter. The infusion balloon has openings in its side wall so that as medication is forced into the balloon from outside the subject it exits the balloon and passes into the blood vessel wall.

An infusion catheter is often used in conjunction with an angioplasty procedure to re-establish normal blood flow in a blood vessel. The infusion catheter is used to deliver drugs which can prevent restenosis or re-blockage of the blood vessel.

Examples of prior art patents relating to infusion catheters are U.S. Pat. No. 5,087,244 to Wolinsky, U.S. Pat. No. 5,232,444 to Just et al., U.S. Pat. No. 5,049,132 to Shaffer et al., U.S. Pat. No. 5,213,576 to Abiuso et al., and U.S. Pat. No. 5,318,531 to Leone. The disclosures of the Abiuso et al and the Leone patents are incorporated herein by reference.

The present invention concerns an improved infusion catheter designed to deliver medication into a subject blood vessel while maintaining adequate blood flow through the vessel.

SUMMARY OF THE INVENTION

The present invention provides an infusion balloon catheter used in combination with an elongated guide wire for injecting drugs and other substances into a blood vessel of a patient.

In accordance with one embodiment of the present invention, the infusion catheter includes an elongated catheter tube having a lumen for delivering a treatment fluid. A proximal end of the catheter tube remains outside the patient and a distal end is placed at a treatment location within the patient's vascular system.

Attached to the distal end of the elongated catheter tube is an inflatable infusion balloon for receiving the treatment fluid that is injected into the lumen of the catheter tube. Upon inflation of the infusion balloon, the treatment fluid is discharged through the balloon wall and into the patient's blood vessel.

According to the invention, a guide wire tube routes a guide wire through a distal part of the balloon catheter for use in positioning the infusion balloon. The guide wire tube includes a longitudinal portion at its proximal end along the elongated catheter tube that has one or more perfusion holes. The perfusion holes allow blood to flow through the guide wire tube once the guide wire has been partially withdrawn so that blood flow continues even after the infusion balloon is inflated.

The use of perfusion holes in the guide wire tube allows blood to flow past the inflated infusion balloon, while treatment fluid is being administered. In the illustrated embodiment the blood actually flows through the inflated infusion balloon.

According to another feature of the invention, the longitudinal portion of the guide wire tube has an exit spaced from a proximal end of the elongated catheter tube that allows rapid exchange of the infusion catheter.

These and other features of the invention will be better understood from a detailed description of alternate embodiments of the invention which are described in conjunction with the accompanying drawings.

BRIEF DESCRIPTION OF THE DRAWINGS

FIG. 1 is a schematic depiction of a guide catheter routing a balloon catheter (either an infusion or a dilation catheter) to a treatment site within a subject blood vessel;

FIG. 2 is a schematic depiction of a first embodiment of an infusion catheter constructed in accordance with the present invention;

FIG. 3 is an enlarged section view of the first embodiment of an infusion catheter constructed in accordance with the present invention;

FIG. 4 is an enlarged cross section view as seen from the plane 4—4 in FIG. 3, showing an infusion lumen and stiffening wire lumen;

FIG. 5 is an enlarged cross section view as seen from the plane 5—5 in FIG98. 3, showing an infusion lumen, guide wire tube, and perfusion holes;

FIG. 6 is a schematic depiction of a second embodiment of an infusion catheter constructed in accordance with the present invention;

FIG. 7 is an enlarged section view of the second embodiment of an infusion catheter constructed in accordance with the present invention; and, FIG. 8 is a cross section view as seen from the plane 8—8 in FIG. 7, showing an infusion lumen, guide wire tube, and perfusion holes.

DETAILED DESCRIPTION OF THE PREFERRED EMBODIMENTS

FIG. 1 illustrates use of a guide catheter 10 for positioning a balloon catheter 12 within a subject blood vessel. The guide catheter 10 includes an elongated body having a central passageway 14 that extends from a fitting 16 outside the subject blood vessel through the elongated body and out the distal end 20 of the guide catheter 10. In most applications, the guide catheter 10 is advanced until the guide catheter's distal end 20 reaches a position within the subject's cardiovascular system close to a treatment region. The treatment region can be the location of a lesion that is to be compressed or can be the location for delivery of a treatment fluid such as heparin. In the former instance a balloon 22 treats the lesion by coming into contact with it and in the latter instance the balloon 22 is only positioned within the blood vessel for delivery of a treatment fluid.

Positioning of the balloon 22 is performed with the aid of a guide wire 26. Before placing the infusion catheter 12 within the guide catheter 10, the guide wire 26 is inserted into and pushed through a guide wire tube 120 at the catheter's distal end (FIG. 2) The guidewire's distal tip extends a few centimeters beyond the balloon catheter's distal end. The combination of the guide wire 26, the balloon catheter 12 and its attached balloon 22 are then inserted into the guide catheter 10 until the end of the guide wire 26 exits the guide catheter 10. Both the guide wire 26 and the balloon 22 are pushed forward until the guide wire 26 tip extends beyond the treatment region and the balloon catheter 12 is properly positioned. Positioning of the balloon 22 is facilitated by use of a marker member attached to the catheter that can be viewed on a monitor by an attending physician. The present invention is principally concerned with use of the disclosed embodiments of the invention for delivering a treatment fluid to a treatment region while allowing continued blood flow through the blood vessel being treated.

FIG. 2 depicts in greater detail one embodiment of an infusion balloon catheter 110 for injecting a fluid into a subject. The infusion catheter 110 includes an elongated catheter tube 112 for delivering a fluid (such as heparin) to an infusion site within a subject. A lumen 114 for injecting the fluid extends from a proximally located fluid input port 116 to a distal end of the elongated catheter tube 112.

Attached to the distal end of the elongated catheter tube 112 is an inflatable infusion balloon 115. The infusion balloon 115 comprises inner and outer fluid confining balloons 130, 132 that together bridge a fluid delivery region within a blood vessel. A first balloon 130 bounds an inner chamber 140. A center wall portion 142 that bounds the inner chamber 140 has openings or holes 144 spaced along the center wall portion 142. At a proximal end 134 of the infusion balloon the two balloons 130, 132 overlap an end of the catheter body 112 to form a fluid entryway or opening 146 in fluid communication with the lumen 114 passing through the elongated catheter body 112. Fluid injected into the input port 116 passes through the lumen 114 from outside a subject into the inner chamber 140 by means of the entryway 146.

An outer chamber 150 is bounded by an outer wall 152 of the second balloon 132. The outer chamber 150 is bounded by an outer surface of the wall 142 that defines the inner chamber 140. The outer wall 152 includes fluid delivery openings 154 spaced outwardly from a center region of the inner chamber wall 142 that defines the holes or openings 144. Fluid exits the inner chamber to the outer chamber by means of these holes 144, passes through the outer chamber 150 and enters the wall of a blood vessel through the delivery openings 154 in the outer wall 152.

At its distal end the elongated catheter 110 includes a guide wire tube 120 for positioning the catheter within the subject. In the FIG. 2 embodiment, the guide wire tube 120 extends completely through the inner chamber 140 and includes distal 122 and proximal ends 124 that open into the blood vessel.

As best shown in FIG. 3, a longitudinal portion of the guide wire tube 120 outside the infusion balloon 115 extends alongside the distal end of the elongated catheter tube 112 and includes a number of perfusion holes 128. The perfusion holes 128, which also extend through a portion of the inner balloon 130, allow continued blood flow through the subject blood vessel while the infusion balloon 115 is inflated, thereby avoiding cut-off of blood flow through the subject vessel.

The guide wire tube 120 defines an exit 126 at its proximal end 124 spaced from the balloon 115 toward a proximal end of the elongated catheter tube 112. The guide wire tube 120 allows for rapid exchange of the catheter with a similar catheter of slightly different dimension without withdrawing the guidewire 26. To exchange catheters, a guidewire 26 is held stationary (the guide wire may have been put in place with some difficulty so it is desirable not to have to withdraw it) and the catheter body 112 is withdrawn over the guidewire 26 until the catheter balloon 115 exits from the guide catheter 10. A portion of the guidewire 26 distal to the catheter balloon 115 can then be grasped by an attending physician and an alternate catheter having a similar guide wire tube can be pushed over the guidewire 26 and inserted back into the guide catheter to position the alternate catheter at a treatment site.

As shown in FIG. 4 of the drawings, the elongated catheter tube 112 comprises a pair of lumens; an infusion lumen 114 which routes the inflation fluid into the balloon, and another second lumen 135 which encloses a metal stiffening wire 136 (see FIG. 3). The stiffening wire 136 may be fixed in place, typically by fusing, within the catheter body 112. This wire 136 extends from the proximal end of the elongated catheter body 112 to a point just behind the exit 126 through which the guidewire 26 exits the catheter body 112. The second lumen 135 may be closed at its distal end 137 typically by fusing, and at its proximal end by a connector 170 that defines the infusion input port 116. As clearly shown in FIGS. 3 and 5 depicting the first embodiment, the perfusion holes 128 are in fluid communication with the inner lumen 125 of the guide wire tube 120.

In accordance with practice of the invention, the balloon 115 is positioned within the patient's blood vessel near a treatment location. During this positioning the guidewire 26 extends completely through the guidewire tube 120. Prior to inflating the infusion balloon 115 with the treatment fluid, the guidewire 26 is partially withdrawn from the guide wire tube 120, but not beyond the guide wire tube exit 126. The treatment fluid is injected into the infusion balloon 115 to inflate the infusion balloon 115. The guide wire tube 120 allows blood to pass through the perfusion holes 128 in the wall of the guide wire tube 120, and, because it extends completely through the inflated infusion balloon, allows continuous blood flow through the holes 128 in the sidewall of the tube 120 while the infusion occurs. Subsequent to the infusion treatment, the balloon 115 is deflated and the guidewire 26 pushed through the guidewire tube 120 and out the distal end 122 of the guidewire tube 120. The catheter 110 may then be withdrawn over the guide wire 26 and, if desired, exchanged with another catheter.

FIGS. 6–8 depict a second balloon catheter 210 having a guide wire tube 220 with perfusion holes 228 for allowing continued blood flow with the catheter's distally located balloon inflated.

The second catheter 210 has an elongated body 211 having a single lumen 212 for injecting treatment fluid into a chamber 213 bounded by an inner balloon 214. Treatment fluid passes through a number of openings 215 into a chamber 216 bounded by an outer balloon 217. The outer balloon 217 has openings 218 that deliver the fluid to the blood vessel. A portion of the inner balloon 214 includes perfusion openings 238 that allow blood to pass through to the openings 228 of the guidewire tube 220. Fabrication of the catheter 210 the guide wire tube 220 and the body 211 are fused together to form an oval shape depicted in FIG. 8. For the second embodiment depicted in FIGS. 6–8, the tube 220 has a proximal end 226 that opens into the subject blood vessel without resort to a bend in the tube lumen 230. This second embodiment has a proximal fitting 240 that is connected to the body 211 that defines an inlet port 242. Although no stiffening wire is shown in this second embodiment such a wire could be employed to control the flexibility of the catheter.

Experience with an infusion catheter constructed in accordance with the present invention suggests certain ranges of values for the dimensions for lengths of the guide wire tubes 120, 220 that extend proximal to the infusion balloon. A preferred length of the guide wire tube 120, 220 that includes perfusion openings 128, 228 should extend 2 to 3 inches from the guide wire tube exits 126, 226 to the proximal end 134, 234 of the outer balloon 132, 217. This length will facilitate proper blood perfusion through the guide wire tube 120, 220 with the guide wire 26, 221 still positioned within the proximal end of the guide wire tube 120, 220 to ensure the guide wire 26, 221 can be reinserted subsequent to infusion.

It has been found through practice of the invention that preferred sizes for the inside diameter of the infusion lumen 114 may typically be about 0.016 to 0.017 inches. For the guide wire tube 120, 220 preferred sizes for the inside diameter may typically be about 0.030 to 0.032 inches, or about twice that of the diameter of the infusion lumen. This preferred guide wire tube 120, 220 diameter allows for a preferred blood flow rate of about 40 cubic centimeters per minute to be maintained while infusion occurs.

While the present invention has been described with a degree of particularity, it is the intent that the invention include all modifications and alterations from the disclosed design falling within the spirit and scope of the appended claims.

What is claimed is:

1. A rapid exchange perfusion and infusion balloon catheter for use in combination with an elongated guide wire to infuse drugs and other therapeutic substances into a blood vessel of a patient, comprising:
   a) an elongated catheter shaft having a lumen for delivering an inflation fluid; said catheter shaft including a proximal end that remains outside the patient and a distal end for placement at a treatment location within the patient's vascular system;
   b) an inflatable infusion balloon attached to and in fluid communication with the distal end of the elongated catheter shaft for receiving inflation fluid injected into the lumen of the elongated catheter shaft to inflate the infusion balloon, wherein the balloon has a cylindrical inflatable portion and a proximal leg and a distal leg attached to the catheter shaft, said inflatable portion having a plurality of apertures providing fluid communication between an interior of the infusion balloon and the blood vessel of the patient, such that said inflation fluid call be delivered along a flow path directly from the lumen of the catheter shaft, into the infusion balloon, and out through the apertures to infuse a desired site in the blood vessel;
   c) a guide wire tube that routes a guide wire through a distal part of the balloon catheter for positioning the infusion balloon; said guide wire tube defining a rapid exchange configuration by having a distal opening at the distal end of the catheter and a proximal opening in communication with an exterior of the catheter shaft, the proximal opening being disposed a relatively short distance proximal front the balloon and a much longer distance distal from the proximal end of the catheter;
   d) wherein the guide wire tube further defines a perfusion configuration by a longitudinal perfusion portion near the proximal end of the guide wire tube and extending along the elongated catheter shaft; said longitudinal perfusion portion of the guide wire tube having a plurality of inner perfusion holes to allow blood to flow through the guide wire tube and out the distal opening of the guide wire tube, after the guide wire has been partially withdrawn such that the distal end of the guidewire is disposed proximal from the perfusion holes; and
   e) wherein the proximal leg of the balloon also has a plurality of outer perfusion holes in positions matching the positions of the inner perfusion holes, thereby enabling the longitudinal perfusion portion of the guidewire tube and the proximal leg of the balloon to overlap.

2. The catheter of claim 1 wherein the apertures are formed as microporous holes spaced along the center of the balloon.

3. The catheter of claim 2 wherein said balloon has a proximal segment attached to a distal portion of the elongated catheter tube and a proximal portion of the guide wire tube.

4. The catheter of claim 3 wherein said balloon has a distal segment attached to a distal portion of the guide wire tube.

5. The catheter of claim 1 where the infusion balloon further comprises an outer balloon attached to and surrounding said infusion balloon, wherein the outer balloon also has a plurality of outer apertures providing fluid communication and allowing infusion of the infusion fluid from within the infusion balloon and out through the outer apertures.

6. The catheter of claim 5 wherein said infusion balloon has a fluid containing lobe at its proximal end and a fluid containing lobe at its distal end, and said lobes are in fluid communication with and are connected by a center section having microporous holes.

7. The catheter of claim 6 wherein said outer balloon is attached to the infusion balloon at the lobes of the infusion balloon, and is spaced from the infusion balloon at said center section, wherein the outer balloon has microporous holes between said fluid containing lobes.

8. The catheter of claim 6 wherein said infusion balloon has a proximal segment attached to a distal portion of the elongated catheter shaft and a proximal portion of the guide wire tube.

9. The catheter of claim 6 wherein said infusion balloon has a distal segment attached to a distal portion of the guide wire tube.

10. The catheter of claim 1 where the infusion balloon comprises an outer sheath attached to an inner balloon.

11. The catheter of claim 10 wherein said infusion balloon has a fluid containing lobe at a proximal end and a fluid containing lobe at a distal end, and said lobes are in fluid communication with and are connected by a center section having microporous holes.

12. The catheter of claim 11 wherein said outer sheath is attached to the infusion balloon at the lobes of the infusion balloon, and is spaced from the infusion balloon at said center section, wherein the outer balloon has microporous holes between said fluid containing lobes.

13. The catheter of claim 11 wherein said infusion balloon has a proximal segment attached to a distal portion of the elongated catheter shaft and a proximal portion of the guide wire tube.

14. The catheter of claim 11 wherein said infusion balloon has a distal segment attached to a distal portion of the guide wire tube.

15. The catheter of claim 1 where the guide wire tube has a larger inside diameter than the outside diameter of a guide wire inserted within the guide wire tube.

16. A method for treating a blood vessel comprising the steps of:
   a) providing a first catheter having an infusion balloon at a distal end with a guide wire tube that extends through the infusion balloon and has proximal and distal guidewire openings disposed both proximal and distal of the infusion balloon, wherein said proximal guidewire opening is spaced a substantial distance distal from a proximal end of the first catheter, and the guidewire tube has inner perfusion holes along a longitudinal portion of a proximal end of the guidewire tube to allow blood to flow through the guidewire tube while the balloon is inflated, wherein an inflatable portion of the infusion balloon has a plurality of infusion apertures, and the infusion balloon further has a proximal leg attached to the guidewire tube with outer perfusion holes in positions matching the positions of the inner perfusion holes;
   b) inserting a guide wire having proximal and distal ends into the patient's blood vessel to a treatment location;
   c) advancing the first catheter over the guide wire until the infusion balloon is at the treatment location;
   d) partially withdrawing the guide wire in a proximal direction, such that the guidewire distal end is moved proximal from the outer and inner perfusion holes, without removing the guidewire completely from the guide wire tube, and allowing blood to perfuse by passing through the outer and inner perfusion holes, through the guide wire tube and out the distal guidewire opening;
   e) injecting therapeutic fluid into the infusion balloon to inflate the infusion balloon and cause the therapeutic fluid to pass through the infusion apertures to infuse the treatment location of the blood vessel;
   f) advancing the guide wire through the guide wire tube until the guide wire distal end is again at the treatment location;
   g) removing the first catheter from the patient and from the guide wire, while retaining the guide wire distal end at the treatment location; and
   h) advancing a second catheter over the guide wire.

17. A method for treating a blood vessel comprising the steps of:
   a) providing a first intravascular catheter having proximal and distal ends;
   b) inserting a guide wire having proximal and distal ends into the patient's blood vessel to a treatment location;
   c) advancing the first catheter over the guide wire until the distal end of the first catheter is at the treatment location;
   d) removing the first catheter from the patient and from the guide wire, while retaining the guide wire distal end at the treatment location; and
   e) providing a second intravascular catheter having an infusion balloon at a distal end, with a guide wire tube that extends through the infusion balloon and has proximal and distal guidewire openings disposed both proximal and distal of the infusion balloon, wherein said proximal guidewire opening is spaced a substantial distance distal from a proximal end of the first catheter, and the guidewire tube has inner perfusion holes along a longitudinal portion of a proximal end of the guidewire tube to allow blood to flow through the guidewire tube while the balloon is inflated, wherein an inflatable portion of the infusion balloon has a plurality of infusion apertures, and the infusion balloon further has a proximal leg attached to the guidewire tube with outer perfusion holes in positions matching the positions of the inner perfusion holes;
   f) advancing the second catheter over the guide wire;
   g) partially withdrawing the guide wire in a proximal direction, such that the guidewire distal end is moved proximal from the outer and inner perfusion holes, without removing the guidewire completely from the guide wire tube, and allowing blood to perfuse by passing through the outer and inner perfusion holes, through the guide wire tube and out the distal guidewire opening;
   h) injecting therapeutic fluid into the infusion balloon to inflate the infusion balloon and cause the therapeutic fluid to pass through the infusion apertures to infuse the treatment location of the blood vessel.

* * * * *